United States Patent [19]

Mai et al.

[11] Patent Number: 4,709,042

[45] Date of Patent: Nov. 24, 1987

[54] PROCESS FOR THE PREPARATION OF 2-(1-HYDROXYALKYL)-5,5-DIPHENYL-HYDANTOIN

[75] Inventors: Khuong H. X. Mai, Waukegan; Ghanshyam Patil, Vernon Hills, both of Ill.

[73] Assignee: E. I. Du Pont de Nemours & Co., (Inc.), Wilmington, Del.

[21] Appl. No.: 909,140

[22] Filed: Sep. 19, 1986

[51] Int. Cl.$^4$ .......................................... C07D 233/72
[52] U.S. Cl. ..................................... 548/312; 548/314
[58] Field of Search ................................ 548/312, 314

[56] References Cited

U.S. PATENT DOCUMENTS 4,163,058 7/1979 Stella et al. ..................... 548/312 X
4,260,769 4/1981 Stella et al. ......................... 548/112

OTHER PUBLICATIONS

March, J. Advanced Organic Chemistry, McGraw Hill, New York, 1968, pp. 667–668.

Primary Examiner—Richard A. Schwartz
Attorney, Agent, or Firm—Gildo E. Fato

[57] ABSTRACT

Described is a process for preparing 2-(1-hydroxyalkyl)-5,5-diphenylhydantoin having the formula

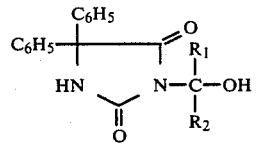

wherein $R_1$, $R_2$ and $R_3$ are each independently hydrogen, $C_1$–$C_{20}$ alkyl, $C_3$–$C_{12}$ cycloalkyl, $C_7$–$C_{15}$ aralkyl, unsubstituted or substituted aryl or heteroaryl or alternatively, or $R_1$ and $R_2$ together with the carbon atom form a 3 to 12 member cycloalkyl group, the process comprising: reacting diphenylhydantoin with an aldehyde or a ketone in the presence of a strong inorganic base; an alcohol was used as solvent to solubilize the reactants. The reaction is practically complete in 15 minutes.

The compounds so prepared are intermediates in the preparation of phenyltoin prodrugs.

6 Claims, No Drawings

PROCESS FOR THE PREPARATION OF 2-(1-HYDROXYALKYL)-5,5-DIPHENYLHYDANTOIN

BACKGROUND OF THE INVENTION

The present invention relates to a novel process for the preparation of 2-(1-hydroxyalkyl)-5,5-diphenylhydantoin, or simply 2-hydroxyalkylphenytoin. This compound is a very important intermediate in the preparation of phenytoin prodrug. U.S. Pat. No. 4,163,058 describes the preparation of this intermediate. The given procedure calls for large amounts of solvent, e.g., water, to solubilize the reactants. The low solubility of phenytoin in water creates an immediate inconvenience due to large volume of solvent and prolonged reaction period.

SUMMARY OF THE INVENTION

In accordance with one embodiment of the present invention, 2-hydroxyalkylphenytoins, were prepared by reacting phenytoin with an aldehyde or a ketone in the presence of an alcohol and a catalytic amount of a strong base, e.g., NaOH.

The process of the invention can be depicted by the following reaction scheme:

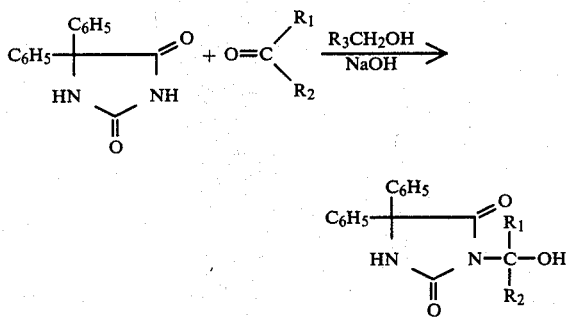

In the above reaction scheme, $R_1$, $R_2$ and $R_3$ are each independently hydrogen, lower alkyl, or $R_1$ and $R_2$ together with the carbon atom form a 3 to 12 member cycloalkyl group.

The term "lower alkyl" as used herein refers to straight or branched chain alkyl radicals containing from 1 to 6 carbon atoms including but not limited to methyl, ethyl, n-propyl, iso-propyl, n-butyl, sec-butyl, tert-butyl, n-pentyl, iso-pentyl, sec-pentyl, tert-pentyl, neo-pentyl and the like.

The term "cycloalkyl" as used herein refers to cyclic saturated aliphatic radicals containing 3 to 12 carbon atoms in the ring, such as cyclopropyl, cyclobutyl, cyclopentyl or cyclododecy.

In the process, phenytoin is added to a solution of an aldehyde or a ketone in an alcohol in the presence of catalytic amount of strong base, e.g., NaOH. A suitable temperature is 20° C. to about 100° C., preferably at ambient temperature and a reaction time from 1 minute to 2 hours, preferably 15 minutes. Suitable solvents are methanol, ethanol, n-propanol, isopropanol, butanol, or a mixture thereof.

In the described method, phenytoin and the carbonyl compound may be theoretically used in an amount of about one equivalent each for the purpose of preparing the 2-hydroxyalkylphenytoin but it is preferable to use an excess amount of the carbonyl compound which functions both as reactant and solvent.

DETAILED DESCRIPTION OF THE INVENTION

In accordance with one embodiment of the present invention, the preparation of 2-hydroxyalkylphenytoins was conducted as follows:

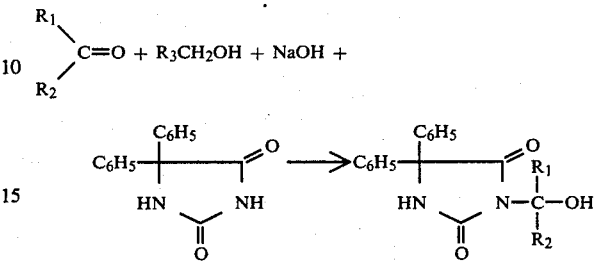

A general procedure is as follows: One (1) kg of phenytoin in one lot was added to a stirred mixture of 1 liter (L) of 37% aqueous formaldehyde, 1 L of ethyl alcohol and 5 g of sodium hydroxide. At the end of the addition, the solution became homogeneous. After one minute, white granulars of 2-hydroxymethylphenytoin started to separate. Stirring was continued for another 15 minutes. Water (1 L) was added and the product filtered, washed with water and air-dried. Yield: 1.01 kg (90%), melting point 184°–186° C.

The process offers the advantage of significantly reduced amount of required solvent in comparison to the process of the prior art and thus provides a convenient, simple and fast procedure for the preparation of 2-hydroxyalkylphenytoin.

What is claimed is:

1. A process of preparing a 2-(1-hydroxyalkyl)-5-5-diphenylhydantoin of the formula

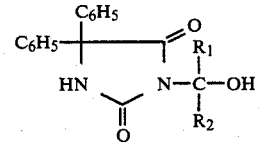

wherein $R_1$ and $R_2$ are each independently hydrogen, $C_1$–$C_6$ alkyl, or $R_1$ and $R_2$ together with the carbon atom to which they are attached form a 3 to 12 member cycloalkyl group, which process comprises: mixing in a single reaction vessel a selected aldehyde or ketone, an alcohol, a catalytic amount of an inorganic strong base, and phenytoin, respectively, in the named order, to produce the desired 2-(1-hydroxyalkyl)-5,5-diphenylhydantoin.

2. The process of claim 1 wherein the mixture is heated at a temperature from about 20° C. to 100° C. for a time up to 2 hours.

3. The process of claim 1 wherein the solvent is selected from a group consisting of methanol, ethanol, propanol, butanol, or a mixture thereof.

4. The process of claim 1 wherein the process is conducted at ambient temperature.

5. The process of claim 4 wherein the solvent is selected from a group consisting of methanol, ethanol, propanol, butanol, or a mixture thereof and wherein the reaction is conducted for a time of from about 1 minute to about 2 hours.

6. The process of claim 5 wherein the process is conducted for a time of about 15 minutes.

* * * * *